United States Patent [19]
Rekker et al.

[11] Patent Number: 5,856,603
[45] Date of Patent: Jan. 5, 1999

[54] PROCESS FOR THE PRODUCTION OF CYCLOHEXANE

[75] Inventors: Tjalling Rekker, Culemborg; Bernard Hendrik Reesink, Bt Doorn; Frederik Borninkhof, Ijsselstein, all of Netherlands

[73] Assignee: Engelhard Corporation, Iselin, N.J.

[21] Appl. No.: 765,763

[22] PCT Filed: Aug. 4, 1995

[86] PCT No.: PCT/US95/09869

§ 371 Date: Jun. 19, 1997

§ 102(e) Date: Jun. 19, 1997

[87] PCT Pub. No.: WO96/06817

PCT Pub. Date: Mar. 7, 1996

[30] Foreign Application Priority Data

Aug. 26, 1994 [EP] European Pat. Off. .............. 94202443

[51] Int. Cl.$^6$ ...................................... C07C 5/10
[52] U.S. Cl. ............................ 585/270; 585/274; 585/276
[58] Field of Search ...................................... 585/266, 268, 585/269, 270

[56] References Cited

U.S. PATENT DOCUMENTS 2,744,052  5/1956  Nozaki ........................................ 196/24
3,859,370  1/1975  Carter et al. ......................... 260/638 B

FOREIGN PATENT DOCUMENTS 787049  2/1957  United Kingdom .

*Primary Examiner*—Bekir L. Yildirim

[57] ABSTRACT

The invention is directed to a process for the production of cyclohexane by catalytic hydrogenation of benzene using hydrogen, said process comprising the hydrogenation of benzene in the presence of a supported nickel catalyst having a nickel content of at least 10 wt. %, calculated as nickel, said catalyst containing sulfur, or compounds thereof, as promotor.

9 Claims, No Drawings

PROCESS FOR THE PRODUCTION OF CYCLOHEXANE

The invention is directed to a process for the production of cyclohexane by catalytic hydrogenation of benzene in the presence of a supported nickel catalyst.

Cyclohexane is an important chemical, especially as intermediate for the production of caprolactam, a monomer for the production of nylon-6. Cyclohexane is produced in huge quantities, mainly by hydrogenation of benzene in the presence of hydrogen, for example in a fixed bed of a (supported) nickel catalyst, or in the presence of a noble metal catalyst. A review of the production of cyclohexane by hydrogenation of benzene has been given in Uhlmanns' Enzyklopädie der technischen Chemie, 4th. ed, Band 9, page 680 ff.

Although the hydrogenation reaction proceeds with good activity and relatively high selectivity (over 99.95% at optimal reaction conditions), there is an increasing interest in reducing the amount of byproducts to a level below the presently obtained level of about 200 ppm. Conventionally the hydrogenation of benzene leads to the production of n-hexane, methyl-cyclopentane, methylpentane, n-pentane and methane as predominant byproducts.

This interest in reducing the amounts of byproducts comes especially from the end users of the nylon-6, who require very low levels of byproducts in the nylon-6 in order to improve the properties of the nylon. One of the methods of decreasing the amount of byproducts in caprolactam and subsequently in the endproduct is the reduction of the amount of byproducts in the cyclohexane.

Reduction of the production of byproducts can usually be obtained by a reduction of the activity, for example by lowering the reaction temperature. However, this leads to an increase in production costs, due to the necessity of larger equipment for the production and/or larger recycle of unconverted benzene. This is accordingly not a preferred option for reduction of the amount of byproducts.

It is an object of the present invention to provide an improved process for the production of cyclohexane by catalytic hydrogenation of benzene in the presence of a supported nickel catalyst.

The invention is based on the surprising feature that promoting the nickel catalyst with sulfur results in an increase of selectivity that is much larger than would be expected on the basis of the decrease of activity. Restoring the activity to the original level, for example by the use of a different method of producing the catalyst, or the use of more nickel, results in a catalyst that still has a higher selectivity than the original unpromoted catalyst of the same activity. Accordingly the use of sulfur as promoting agent for the catalyst improves the ratio of selectivity to activity.

Additionally it has been noted that surprisingly the life time of the catalyst is increased. The life time of a catalyst is also a function of activity. At the same activity the catalyst life time is generally increased.

Accordingly the invention concerns a process for the production of cyclohexane by catalytic hydrogenation of benzene using hydrogen, said process comprising the hydrogenation of benzene in the presence of a supported nickel catalyst having a nickel content of at least 10 wt. %, calculated as nickel, said catalyst containing sulfur, or compounds thereof as promotor.

The amount of the promotor can be selected within wide ranges. The lower limit of the amount is determined by the minimal amount required to give a reasonable improvement, which improvement is especially influenced by the atomic promotor to nickel ratio. This means that at higher nickel amounts the amount of promoter will usually be higher. The suitable catalysts are usually promoted with sulfur in an atomic sulfur/nickel ratio of between 0.01 and 1, preferably between 0.02 and 0.5. The level of sulfur in the catalyst can be used to tune the activity to the required value. As each type of benzene hydrogenation process requires different activity, for example due to different reactor geometry and heat exchange capacity, the promotor amount may be varied to meet the requirements of the actual process, within the ranges specified above. In all cases the ratio of activity and selectivity will be improved for the promoted catalysts. In the figure accompanying the examples this effect of improved activity is shown.

It is remarked that promoting nickel catalysts with sulfur has been known for some time. These catalysts are mainly used for hydrogenation of triglycerides, more in particular to obtain hydrogenation products having certain advantageous properties, usually at the expense of activity.

From U.S. Pat. No. 3,856,831 it is known to hydrogenate fats and oils with a nickel catalyst which has been partially poisoned with sulfur. Such catalysts are sometimes referred to as poisoned with sulfur or promoted with sulfur. The problem is that when sulfur is added to the catalysts, active sites that would normally be available for dissociation of hydrogen are irreversibly occupied by sulfur. This leads to a lower degree of hydrogen coverage, which yields an increased degree of isomerization, in addition to a lower hydrogenation activity.

In EP-A 464,956 a sulfur promoted catalyst has been described especially for slurry phase hydrogenation of triglycerides, which catalyst has very good filterability. This catalyst is supported on alumina and has an atomic S/Ni ratio of between 0.06 and 0.10, and an atomic Ni/Al ratio of between 2 and 10. This catalyst is very suitable for selective hydrogenation of oils to mono-unsaturated triglycerides having a steep melting range.

British patent specification No. 787,049 describes so-called sulfactive catalysts for hydrogenation of various petroleum oils, said catalyst consisting of cobalt/molybdenum or nickel/molybdenum on alumina, which catalysts are used in sulfided form, i.e. at last half of the metal atoms have been sulfided. The nickel content of those catalysts is kept very low, namely below 10 wt. %.

Suitable catalysts for the process of the present invention are the conventional supported catalysts having a nickel content of 10 wt. % or more, calculated as nickel, which are promoted with sulfur. Generally the nickel content may range from 10 to 95 wt. %, calculated as nickel on the weight of the catalyst. Preferred lower limits for the nickel content, depending on the required activity and the type of process used, are 15 resp. 20 wt. %. A suitable upper limit for the amount of nickel is 80 wt. %. In general a nickel content between 50 and 80 wt. % is preferred. The nickel contents are all based on the final, activated (reduced) catalyst. The catalyst can optionally be promoted with other metals, the amount of promotor being less than 5 wt. %, based on the combined weight of the nickel and the promotor metal. In a preferred embodiment nickel is the only metal present.

As support it is preferred to use one or more refractory oxides, or active carbon, whereby of the refractory oxides silica, alumina, titaniumoxide, zirconia, alumina, or combinations thereof are preferred, although other supports are not excluded. More in particular it is preferred to use silica, alumina or combinations thereof as support.

The BET surface area of the final catalyst, as defined by S. Brunauer et al., in J.A.C.S. 60, 309 (1938) is generally between 50 and 500 m$^2$/g for refractory oxides, as within these ranges an optimal balance between activity and selectivity is obtained. For the same reason the BET surface area of active carbon is preferably not more than 1500 m²/g.

The optimal results in terms of improvement of selectivity in relation to activity is obtained with shaped, fixed bed catalysts containing 50–80 wt. % nickel in the reduced catalyst, on a support of silica and alumina, which catalyst has been promoted with sulfur in an atomic sulfur to nickel ratio between 0.01 and 0.1.

The catalysts to be used according to the invention can be prepared in various ways, but it is preferable to use a process comprising deposition precipitation of nickel on a solid support, coprecipitation techniques, impregnation techniques (such as incipient wetness impregnation) under such conditions that a precursor of a supported nickel catalyst is formed, followed by separating the catalyst or precursor from the liquid, drying and optional calcination and/or activation, with a sulfur compound being applied to the catalyst during or after the formation referred to.

In the preparation of the catalysts, a solution of a nickel compound having a pH $\leq 6$ may be used. Preferably the pH is between 4 and 6. Suitable nickel compounds are nickel chloride, nickel sulfate, and nickel nitrate.

In the preparation, the morphology of the catalyst can be influenced by the choice of the different variables, such as rate of stirring, temperature, injection rate and the like. These variables are known per se and the skilled worker can determine the appropriate conditions for the desired final result by means of simple tests.

In the literature, various processes have been described for applying sulfur to nickel catalysts. The process described in the aforementioned U.S. Pat. No. 3,856,831 comprises treating a reduced nickel catalyst with a mixture of hydrogen and hydrogen sulfide.

According to U.S. Pat. No. 4,118,342, mixtures of hydrogen and thiophenes or mercaptans are used.

Adding the sulfur compound can also be accomplished during the formation of the catalyst. According to Netherlands patent applications 7,300,719 and 7,201,330, use is made of flowers of sulfur and a sulfur-providing organic compound such as thioacetamide, respectively, during precipitation of the catalyst.

Application of the sulfur compound, is preferably accomplished using a water-soluble sulfur compound. Suitable sulfur compounds are alkali metal sulfides such as sodium sulfide.

The preference for water-soluble sulfur compounds, and more particularly for sodium sulfide, is based on the ready application thereof, and the eminent reproducibility of the sulfur distribution obtained.

It is also possible, however, to use other sulfur compounds which are described in the prior art, such as flowers of sulfur, thioacetamide, thiophenes and mercaptans. It is also possible to use $H_2S$.

The final catalyst preferably contains sulfur in an atomic sulfur/nickel ratio of between 0.01 and 1, more in particular between 0.02 and 0.5.

The hydrogenation is carried out in the conventional way, under the conditions known in the art If necessary the skilled worker may want to modify the conditions like pressure temperature, amount of hydrogen and the like, by simple tests to obtain the optimal conditions.

Suitable total pressures are between 3 and 150, preferably between 10 and 50 bar; temperatures may be between 100° C. and 350° C. in liquid phase and/or gas phase. In the case of fixed bed hydrogenation the catalyst will be present in the form of shaped catalyst particles, such as granules, pellets, extrudates and the like. Suitable sizes are between 0,5 mm and ½ inch, preferably from ¹⁄₃₂ to ⅛ inch. The physical strength of the catalyst particles is of course sufficient to withstand the forces exerted by a fixed bed.

The invention is now elucidated on the basis of some examples, which are not intended to limit the invention.

EXAMPLES 1–2 (COMPARATIVE)

A nickel catalyst A supported on silica and alumina was prepared by deposition precipitation. Following precipitation the catalyst precursor was washed, separated from the liquid and dried at 110° C. The dried catalyst precursor was calcined in air at 375° C. Subsequently the catalyst precursor was shaped into extrudates with 10% clay as binder and activated using hydrogen, followed by stabilization in air. The nickel content of the final catalyst A was 62.5 wt. %. A second sample was prepared by diluting the catalyst precursor with an inert material, thereby, after shaping into extrudates and activation, obtaining catalyst B with a nickel content of 15 wt. %. Because of the presence of less active material per reactor volume, this catalyst will have a lower activity and, consequently, an improved selectivity.

The catalysts were used for benzene hydrogenation in a 1.0 ml micro-reactor using a 0.2 ml sieve fraction (0,25<dp<0,60 mm) of the granulated catalysts. In order to minimize heat production and thus to avoid excessive byproduct formation, only 0.2 ml of catalyst was used which was diluted to 1.0 ml with α-alumina. The catalysts were re-activated in hydrogen (GHSV 15000 hr⁻¹) for two hours at 250° C.

The activity of the catalysts was evaluated by purging the catalyst bed with a 6 volume % benzene in hydrogen flow (GHSV 9000 hr⁻¹) at temperatures ranging from 50° C. to 150° C. From the resulting Arrhenius plot, which was construed assuming first order rate kinetics, the reaction rate constant was determined at 150° C., if necessary by extrapolation. The relative activity of the catalysts was expressed as the ratio of k (catalyst) to the k of a reference catalyst.

The amount of byproducts formed was measured by using a similar, non-diluted 1.0 ml catalyst bed which was re-activated according to the same procedure as described above. The catalyst bed was purged with a 6 vol % benzene in hydrogen flow (1800 hr⁻¹) at temperatures ranging from 160° to 320° C. The reaction products were analyzed by GC. The selectivities of the catalysts were expressed as the amount of total byproducts formed at 260° C. relative to a reference catalyst whereby less byproduct formation indicates a better selectivity. The results thus obtained are listed in the accompanying table, From this table it follows that catalyst B, due to its lower nickel content per catalyst volume has a significant lower (relative) activity and, consequently, produces much less byproducts compared to catalyst A

EXAMPLES 3 AND 4

Sulfur promoted nickel on alumina and silica catalysts C and D, with an atomic sulfur/nickel ratio of 0,021 and 0,034 respectively, were prepared by adding the appropriate amounts of sodium sulfide during precipitation of the catalyst precursor. The relative activity of the catalyst (in relation to the same reference catalyst as used for examples 1 and 2) was further steered to a level of between 1 and 4 by selection of suitable activation conditions. The nickel contents of the final catalysts C and D were 61.3 wt. % and 64.1 wt. % respectively. The activity and selectivity of the catalysts C and D were determined and described previously in example 1 and listed in the table.

From the results in the table it follows that catalyst D, at the same activity level, produces less byproducts compared to the non-promoted catalyst B. Moreover, even catalyst C with higher activity produces less byproducts in the above described benzene hydrogenation test.

EXAMPLE 5

Catalyst E was prepared by diluting the precursor material of catalyst C (example 3), having an atomic sulfur/alumina ratio of 0,021, with an inert material prior to forming the catalyst. Thus, after activation with hydrogen under suitable process conditions, catalyst E was obtained with a nickel content of 45.1 wt. %. Compared to catalyst B this catalyst also produces less byproducts during benzene hydrogenation at a slightly higher activity level. It is to be noted that the amount of byproducts obtained with catalyst E is not less than catalyst C although it was expected that reduction of the nickel content and thus the activity would result therein. An explanation might be that the level of byproducts is so low that errors in the analysis are responsible for this effect.

|  | Catalyst A | Catalyst B | Catalyst C | Catalyst D | Catalyst E |
|---|---|---|---|---|---|
| Ni % | 62.5 | 51 | 61.3 | 64.1 | 45.1 |
| S/Ni ratio | — | — | 0.021 | 0.034 | 0.021 |
| Rel. Act. | 16 | 1.4 | 3.8 | 1.4 | 1.8 |
| Rel. byprod | 50 | 1.3 | 0.3 | 0.1 | 0.7 |

We claim:

1. A process for the production of cyclohexane, said process comprising the hydrogenation of benzene in the presence of a catalyst consisting essentially of nickel and sulfur or compounds thereof, said catalyst having a nickel content of at least 10 wt. % calculated as nickel.

2. Process according to claim 1 wherein the catalyst has been promoted with sulfur in an atomic sulfur/nickel ratio of between 0.01 and 1, preferably between 0.02 and 0.5.

3. Process according to claim 1 or 2, wherein the support is selected from the group of refractory oxides and active carbon.

4. Process according to claim 2 or 1, wherein the nickel content of the catalyst is between 10 and 80 wt. %, preferably between 50 and 80 wt. % calculated as nickel in the reduced catalyst.

5. Process according to claim 2 or 1, wherein the hydrogenation is carried out at a temperature between 100 and 350° C. and at a total pressure between 3 and 150 bar.

6. Process according to claim 2 or 1, wherein the hydrogenation is carried out in a fixed bed of preformed catalyst particles.

7. Process according to claim 3, wherein the support is selected from silica, alumina, silica-alumina, titania, zironia, and combinations of two or more of these oxides.

8. Process according to claim 7, wherein the support is selected from silica, alumina and combinations thereof.

9. A process for the production of cyclohexane consisting of the catalytic hydrogenation of benzene with a catalyst consisting essentially of nickel and sulfur or compounds thereof, said catalyst having a nickel content of at least 10 wt. % calculated as nickel said process comprising:

a) a pressure of between 3 and 150 bar;

b) a temperature of between 100° C. and 350° C.;

c) a liquid or gas phase;

d) utilizing catalyst particles in the shape of granules, pellets or extrudates in the size range from 1/100 inch to ½ inch; and e) recovering the cyclohexane so produced.

* * * * *